(12) United States Patent
Heron et al.

(10) Patent No.: US 11,480,563 B2
(45) Date of Patent: Oct. 25, 2022

(54) MEDICAL TEST CARD

(71) Applicant: TESTCARD LTD., Brompton BY Sawdon (GB)

(72) Inventors: Luke Heron, Brompton By Sawdon (GB); Andrew Botham, Brompton By Sawdon (GB)

(73) Assignee: TestCard Ltd., Brompton (GB)

( * ) Notice: Subject to any disclaimer, the term of this patent is extended or adjusted under 35 U.S.C. 154(b) by 726 days.

(21) Appl. No.: 16/364,039

(22) Filed: Mar. 25, 2019

(65) Prior Publication Data
US 2020/0309769 A1    Oct. 1, 2020

(51) Int. Cl.
| | | |
|---|---|---|
| *G01N 33/52* | (2006.01) | |
| *G01N 21/25* | (2006.01) | |
| *G01N 21/29* | (2006.01) | |
| *G01N 33/569* | (2006.01) | |
| *G01N 33/68* | (2006.01) | |
| *G01N 33/53* | (2006.01) | |
| *G01N 33/574* | (2006.01) | |

(52) U.S. Cl.
CPC ........... *G01N 33/52* (2013.01); *G01N 21/251* (2013.01); *G01N 21/29* (2013.01); *G01N 33/5308* (2013.01); *G01N 33/56911* (2013.01); *G01N 33/574* (2013.01); *G01N 33/68* (2013.01)

(58) Field of Classification Search
None
See application file for complete search history.

(56) References Cited

U.S. PATENT DOCUMENTS

2001/0012637 A1   8/2001  Casterlin et al.
2003/0175993 A1*  9/2003  Toranto ............. A61B 10/0051
                                                          435/7.1

(Continued)

FOREIGN PATENT DOCUMENTS

| GB | 2511760 | 9/2014 |
| WO | 2005117556 | 12/2005 |
| WO | 2015070750 | 5/2015 |

OTHER PUBLICATIONS

International Search Report and Written Opinion from related PCT Application No. PCT/IB2019/000557, dated Sep. 17, 2019, 15 pages.

*Primary Examiner* — Lore R Jarrett
(74) *Attorney, Agent, or Firm* — Brooks, Cameron & Huebsch, PLLC (57) ABSTRACT

Medical test cards for detecting analytes are provided including a substantially planar body, an analyte detection means, an opening feature, and an optical code. The analyte detection means is enclosed within the planar body and is configured to provide a colorimetric change when a portion of the analyte detection means is contacted with the analyte. The opening feature is configured to provide access to the analyte detection means and the optical code includes information identifying the analyte detection means. Uses of such medical test cards include accessing the analyte detection means enclosed within the planar body by using the opening feature and contacting the analyte detection means with the sample. The optical code is read using an imaging device to identify the analyte detection means and the analyte detection means is imaged following contact with the sample using the imaging device.

18 Claims, 7 Drawing Sheets

(56) References Cited

U.S. PATENT DOCUMENTS

| | | | | |
|---|---|---|---|---|
| 2009/0253119 | A1* | 10/2009 | Zhou | G01N 33/558 |
| | | | | 435/5 |
| 2009/0263854 | A1* | 10/2009 | Jacono | G01N 33/558 |
| | | | | 435/29 |
| 2011/0150705 | A1* | 6/2011 | Doyle | B01L 3/5055 |
| | | | | 264/328.8 |
| 2012/0262716 | A1* | 10/2012 | Wang | G01N 21/8483 |
| | | | | 356/432 |
| 2013/0330831 | A1* | 12/2013 | Morrow | G01N 21/78 |
| | | | | 436/169 |
| 2014/0072189 | A1* | 3/2014 | Jena | A61B 5/6898 |
| | | | | 382/128 |
| 2014/0273189 | A1* | 9/2014 | Ma | G01J 3/0283 |
| | | | | 435/287.2 |
| 2015/0099307 | A1* | 4/2015 | Bartolome | G01N 21/8483 |
| | | | | 436/95 |
| 2016/0025670 | A1* | 1/2016 | O'Reilly | G01N 33/521 |
| | | | | 204/400 |
| 2016/0080548 | A1* | 3/2016 | Erickson | H04M 1/72409 |
| | | | | 455/556.1 |

\* cited by examiner

MEDICAL TEST CARD

CROSS-REFERENCE TO RELATED APPLICATIONS

This application claims the benefit of U.S. Provisional Application No. 62/621,214, filed on Jan. 24, 2018. The entire disclosure of the above application is incorporated herein by reference.

FIELD

The present technology relates to a medical or diagnostic test card, including a medical or diagnostic test card providing near-patient diagnostics for use by at-home users and/or by healthcare professionals.

INTRODUCTION

This section provides background information related to the present disclosure which is not necessarily prior art.

Detecting various analytes in various bodily fluids and complex mixtures has numerous applications in biological research and clinical diagnostics. Quantifying analytes can extend analysis beyond identifying the presence of an analyte in a bodily fluid, allowing one to elucidate the extent of analyte changes in a bodily fluid or ascertain where certain predefined limits or thresholds are exceeded. Various analytes and/or properties associated therewith can be used as biomarkers of various physiological or disease states. For example, analytes can include one or more metabolic products, small molecules, proteins including various enzymes having various catalytic activities, nucleic acids, pathogens including portions or metabolic products thereof, and synthetic compounds including various drugs or pharmaceuticals. Analytes can be directly or indirectly detected using various affinity, activity, or reactivity relationships, including various binding or coupling events, chemical reactivities, and/or enzymatic activities.

Detection of analytes can be coupled with various quantitation modalities, including various colorimetric reporters, including fluorescent and chemiluminescent reporters. A colorimetric value can be correlated to a particular quantity of the analyte, which can be referenced to standards and/or normalized with respect to certain values. Antibodies, aptamers, nucleic acid hybridization, and other affinity based reagents can be used in various assays for detecting various analytes in molecular diagnostics and research. Particular examples include detecting white blood cells, nitrites, and/or bacteria to identify a urinary tract infection, detecting and quantifying glucose for diabetics, colorimetric assays for detecting pH of bodily fluid, detecting one or more nucleic acids bearing oncogenic mutations in blood, urine, saliva, and other body fluids correlated with the incidence of certain types of cancers, and detecting certain protein analytes (e.g., prostate-specific antigen, interleukins, etc.) in characterizing and identifying certain clinical and research conditions. Levels of small molecules and/or metabolites thereof can likewise be detected and quantified to provide information about health and drug processing in a biological system.

A variety of diagnostic kits are available for detecting various analytes in a patient's bodily fluid, such as urine, blood, saliva, tears, perspiration, and semen, for example. Such kits can be configured to include an object or portion for collecting or contacting the bodily fluid; for example, in the case of saliva, a stick can be provided having an absorbent material at a tip intended for being introduced in the patient's mouth. The kit can also include another portion that stores the bodily fluid sample and allows dispensing to or contacting with an analysis medium where detection and optional quantitation of the analyte occurs. Alternatively, the collecting portion can include the analysis medium. Furthermore, where the volume of bodily fluid can be limiting, the kit further include a portion storing or wetted with a buffer in which the bodily fluid is introduced to combine the bodily fluid with the buffer including various detection and/or reporter components of the kit. Certain types of detection kits can employ various reagent strips including reagents for directly or indirectly detecting the analyte of interest, where certain detection means can be coupled with various quantitation modalities. Examples include reagent strips based on the lateral-flow principle. Detection kits, including those designed to quantify the analyte, can hence be provided the form of various testing strips or sticks, also known as dipsticks, that are contacted with the bodily fluid.

Depending on the nature of the detection kit, certain limitations can be associated therewith. For example, one longstanding limitation of many research and diagnostic tests involves resolving differences in the location of the patient versus the location of the detection kit, where the patient may have to travel to a healthcare facility to have the patient's bodily fluid collected and tested using the kit by a trained healthcare professional. Travel and distance, including the involvement of one or more healthcare professionals, can present geographical as well as economic barriers with respect to using such kits as part of a healthcare system. Privacy and social concerns exhibited by patients can also impact a patient's willingness to participate in research or diagnostic testing and can present a barrier with respect to both one-time testing as well as with compliance to a testing or monitoring regime. Configuration of detection kits can also present environmental concerns, where dipsticks and lateral flow testing kits can employ a large degree of materials and packaging, inefficient storage/shipping space, and can generate an undesirable amount of waste.

Accordingly, there is a need to provide a detection kit that addresses such barriers and shortcomings.

SUMMARY

The present technology includes articles of manufacture, systems, and processes that relate to a medical test card for detecting and optionally quantifying one or more analytes. The medical test card can take the form of a postcard to allow mailing of the medical test card between a healthcare facility and a patient. In this way, the patient can receive the medical test card at the patient's location, test the appropriate bodily fluid using an analyte detection means associated with the medical test card, and determine an output of the analyte detection means using an imaging device, such as a smartphone. The medical test card can also be mailed to the healthcare facility for further processing, confirmation, and/or quantitation of the output of the analyte detection means.

Medical test cards for detecting an analyte can include a planar body, an analyte detection means enclosed within the planar body, and an opening feature in the planar body. The planar body can be configured as a postcard that includes a portion for applying or displaying postage and another portion for applying or displaying a mailing address. The analyte detection means can be configured to provide a colorimetric change when a portion of the analyte detection means is contacted with the analyte. The opening feature can be configured to provide access to the analyte detection means enclosed within the planar body. Operation of the opening feature can result in a strip of the body extending from a remainder of the body. The analyte detection means can be coupled to a face of the strip of the body that formed at least a portion of the enclosure. A seal can be included that covers the analyte detection means when the analyte detection means is coupled to the face of the strip of the body that formed at least the portion of the enclosure. An optical code including information identifying the analyte detection means can be included with the medical test card and can be located on the face of the strip of the body that formed at least the portion of the enclosure. A reference standard can be included with the medical card and can be located on the face of the strip of the body that formed at least the portion of the enclosure. It is also possible to include a plurality of the analyte detection means enclosed within the planar body and a plurality of the opening features, where each of the opening features is configured to provide access to one of the analyte detection means enclosed within the planar body.

Medical test cards provided herein can be used in various ways to detect and optionally quantify an analyte in a sample. The analyte detection means enclosed within the planar body can be accessed using the opening feature and the analyte detection means can be contacted with the sample. The optical code can be read using an imaging device to identify the analyte detection means and the analyte detection means can imaged with the imaging device following contact of the analyte detection means with the sample. Examples of imaging devices include various hand-held imaging devices, such as a tablet or smartphone.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology provides medical test cards and uses thereof that improve patient access to diagnostic and research testing, minimize geographical and economic barriers related to such testing, and reduce the environmental impact of such testing. Medical test cards provided herein can be personally employed by a patient, for example at a patient's domicile, and can alleviate privacy and social concerns that a patient may have related to medical testing. Introduction of the medical test cards into a healthcare system can accordingly optimize diagnostic coverage, compliance, and care aspects of the healthcare system.

Embodiments of a medical test card for detecting and optionally quantifying an analyte in accordance with the present technology can include a planar body, an analyte detection means, an opening feature, and an optical code. The planar body can be configured as a postcard and can include a portion for applying or displaying postage and can include another portion for applying or displaying a mailing address. The analyte detection means can be enclosed within the planar body, where the analyte detection means can be configured to provide a colorimetric change when a portion of the analyte detection means is contacted with the analyte. For example, the colorimetric change can be a visible light color change, including a fluorescent or luminescent change in electromagnetic radiation that can be captured by an imaging device; e.g., a digital camera. The opening feature can be located in the planar body and can be configured to provide access to the analyte detection means enclosed within the planar body. The optical code can include information identifying the analyte detection means; e.g., a Quick Response (QR) code.

The medical test card can be configured to have various numbers and/or types of analyte detection means. For example, the medical test card can include a plurality of the analyte detection means enclosed within the planar body. Each of the analyte detection means can be the same or each of the analyte detection means can be different in various embodiments. The medical test card can also be designed with a plurality of the opening features, where each of the opening features can be configured to provide access to one of the analyte detection means enclosed within the planar body.

Various configurations of the analyte detection means and associated opening features can be employed. For example, the opening feature can include a pull tab, where operation of the opening feature can result in a strip of the body extending from a remainder of the body. The analyte detection means can be coupled to a face of the strip of the body that formed at least a portion of the enclosure. A seal can be provided that covers the analyte detection means coupled to the face of the strip of the body that formed at least the portion of the enclosure. The seal can be removed to expose the analyte detection means for contact with a sample to determine whether the sample includes the analyte of interest. The strip of the body can also be detachable from the remainder of the body of the medical test card. Alternatively, a foil seal portion can cover a portion or all of the body on which the analyte detection means is provided, such that a user can peel away the foil seal portion or tear the foil seal potion. In certain embodiments, the optical code can be located on the face of the strip of the body that formed at least the portion of the enclosure and/or a reference standard can be located on the face of the strip of the body that formed at least the portion of the enclosure. In this way, an imaging device can scan the optical code, thereby identifying the analyte detection means associated therewith, and image the analyte detection means following contact with the sample. The imaging device can likewise image the reference standard, which can be used to quantify a colorimetric change in the analyte detection means.

Methods of detecting an analyte in a sample are provided that employ the various embodiments of medial test cards described herein. Such methods can include providing one or more such medical test cards for detecting the analyte. The analyte detection means enclosed within the planar body can be accessed using the opening feature and the analyte detection means can be contacted with the sample.

Various methods can include imaging of an optical code of the medical test card, a reference standard, and/or the analyte detection means when the colorimetric change results from the sample including the analyte. In particular, such methods can include reading the optical code using an imaging device to identify the analyte detection means. Likewise, the analyte detection means can be imaged using the imaging device following contact of a portion of the analyte detection means with the sample. Contact of a portion of the analyte detection means with the sample accordingly provides the colorimetric change when the sample includes the analyte. An image of the colorimetric change can therefore be indicative of the analyte in the sample. Alternatively, the analyte detection means may be operable to undergo either a colour change and/or a result marking process when exposed to bodily fluids (e.g. urine or other bodily fluids). For example, a lateral flow test could be provided as the analyte detection means operable to undergo a result marking process. In a further alternative, the analyte detection means may be a pad operable to have a blood spot applied following a finger prick test and which pad is operable to undergo a colour change reaction. Examples of the imaging device include various digital cameras, devices including or communicating with a camera, handheld imaging devices, various tablets and smartphones, etc.

The image of the analyte detection means can be used in various ways. For example, the image of the analyte detection means can be transmitted from the imaging device to a healthcare provider, remote server, or other location distinct from the medical test card. In an alternative example, processing of the image of the analyte detection means can be performed on a mobile device which also functions as the imaging device. It can be determined whether the image of the analyte detection means includes the colorimetric change and hence detection of the analyte can be reported when the image of the analyte detection means includes the colorimetric change. Reporting detection of the analyte can include a notification on the imaging device and/or a notification sent to a healthcare provider, remote server, or other location distinct from the location of the medical test card.

Methods of using the medical test card can include quantifying the analyte. In particular, such methods can include reading the optical code using an imaging device to identify the analyte detection means, imaging the analyte detection means following contact thereof with the sample, where the imaging can include imaging a reference standard located on a portion of the medical test card using the imaging device, and determining whether the image of the analyte detection means includes the colorimetric change. When the colorimetric change is present, such methods can include comparing the colorimetric change to the reference standard to quantify the analyte and reporting an amount of the analyte. For example, the reference standard can include a series of colors representing a series of colorimetric changes corresponding to a series of analyte concentrations or amounts. In this way, an image of the colorimetric change of the analyte detection means and the reference standard can more accurately quantify the analyte in the sample. Exposure and capture of the analyte detection means and the reference standard in an image therefore can account for environmental conditions presented to the camera and operational parameters of the camera. Put another way, an image including both the colorimetric change of the analyte detection means and the reference standard (e.g., series of colors) is effectively "normalized" for the image capture conditions and the imaging device specifications. This can optimize quantitation of the analyte in a sample when using a particular imaging device.

Where the imaging device has processing means, such as where the imaging device is a smartphone or mobile device with a camera and processor, an application running on the device can be used as a controller/reader in the diagnostic testing methods described herein. The imaging device can read the optical code to identify the analyte detection means of different types of test cards having different types of analyte detection means as well as different types of analyte detection means contained in a single test card. The imaging device can therefore determine whether the image (or a portion thereof) includes a test card and, if so, can apply an image transformation to rectify the input image (e.g., to correct for skew, differences in size between images, and the like). The imaging device can also identify a specific analyte detection means or test for which the test card includes a result (e.g., colorimetric change of the analyte detection means) and the result of that test based on the rectified input image. The test card can be read substantially as described above with regard to the imaging device. Other embodiments include a system having a mobile imaging device and a diagnostic server that operate together to read and analyze one or more test cards. For example, a smartphone can be used to image the optical code and the analyte detection means after contact with the sample and wirelessly send the image to a remote server, where the remote server ascertains the optical code to identify the particular analyte detection means, determines whether the image of the analyte detection means includes the colorimetric change, and when the colorimetric change is present, compares the colorimetric change to the reference standard to quantify the analyte and reporting an amount of the analyte. The same analysis and quantitation can accordingly be performed remotely by the server and/or by the smartphone.

The medical test card can be configured as a traditional postcard embedded with one or more analyte detection means in the form of various testing strips or sticks, also known as dipsticks, that are contacted with the bodily fluid. For example, a test strip including the analyte detection means can be partially or completely removed from the medical test card for use. In certain embodiments, it can be more convenient to remove the test strip including the analyte detection means to contact the analyte detection means with the sample inside of a sample container or where the analyte detection means is placed within a stream of fluid (e.g., urine stream). The unique configuration of the test card facilitates a simple and highly effective delivery mechanism of various analyte detection means for various diagnostic tests, retains the integrity of the test strips including the analyte detection means while in transit, and provides an ease of use that allows non-medically trained individuals to obtain direct diagnosis and insights into health or condition status of themselves or others without the requirement of visiting a doctor or hospital. Using the accompanying mobile application on a smartphone, for example, the present technology can transform the mobile device's camera into an imaging device or scanner and determines the presence of and reads the colorimetric change of the analyte detection means to provide an immediate result/diagnosis on the smartphone's screen.

The present technology can be configured as a postcard providing water resistant or substantially waterproof seals of the analyte detection means contained therein to allow secure delivery (protected from moisture and tampering) of discrete medical diagnostic solutions in a near-patient testing environment. The present technology notably can improve the provision of near-patient testing by making it more accessible to users and hence can provide several benefits and advantages, which can include addressing or overcoming the following geographical, economic, social, and environmental aspects and barriers.

The medical test card can be easily delivered to remote locations where healthcare is difficult to obtain. Access to healthcare can be expensive, where the present technology provides a reliable lost-cost solution for diagnostics to determine whether further healthcare should be sought. The medical test card can provide a decision support mechanism for healthcare providers to determine the "next-step" and/or in the support of pathways laid down by the world health organization (WHO), National Institute for Health and Care Excellence (NICE), other national bodies, or local decision makers. This can provide significant opportunity for efficiencies in "patient-flow", referral reduction/rationalization, pathology testing, drug prescribing, as well driving down the grade/level of staff that could be used for such assessments.

Some health conditions or testing needs carry with them a social stigma (e.g., sexual health and drug testing). In some nations and cultures, the range of health conditions and testing needs that carry a social stigma is much larger. The present technology provides a testing option that can be carried out in confidence in safety, security, and privacy (e.g., the patient's residence). Mental health concerns often limit access to healthcare as certain behaviors exhibited when attending clinics or doctors' offices are often considered unacceptable. Moving those with mental-health conditions from an unfamiliar location where they feel unsafe, which can ultimately impact the integrity of the results, to more familiar locations (e.g., the patient's home), can deliver more accurate results with minimal discomfort.

The frail and those receiving care in their home often require assessments of health in diagnosis and/or monitoring of long term health conditions. Moving these individuals to a healthcare setting can introduce confounding factors in diagnosis and be distressing for the individual. Separating a sample from a patient can further introduce significant governance, tracking, and/or sample quality concerns. The present technology provides a testing option that can be carried out in confidence in the safety, security, and privacy of a private residence and deliver a greater level of accuracy. The present technology, in addition to improving the provision and quality of near-patient testing to home-users or by healthcare professionals, also provides a form factor that home users will find familiar and comforting and thus improve uptake. The improved uptake of well-controlled high-quality testing in the home has the potential to dramatically improve healthcare outcomes.

The medical test card can minimize packaging and optimize transport of diagnostic services. By delivering diagnostic and/or research testing in this form, the medical test card can help reduce waste, can be formed in part of recycled and/or recyclable materials, and the use of plastics or other materials with environmental or disposability concerns can be minimized. Delivery and transport of the medical test card can also be integrated into existing standardized postal delivery systems.

EXAMPLES

Example embodiments of the present technology are provided with reference to the several figures enclosed herewith.

With reference to FIGS. 1-11, a first embodiment of a medical test card 100 is shown that includes a planar body 105, three analyte detection means 110, three opening features 115, and three optical codes 120. Each analyte detection means 110 is enclosed within the planar body 105. Each analyte detection means 110 is configured to provide a colorimetric change when a portion of the analyte detection means 110 is contacted with the analyte (e.g., a sample including the analyte). Each opening feature 115 in the planar body 105 is configured to provide access to a respective one of the analyte detection means 110 enclosed within the planar body 105. Each optical code 120 includes information identifying a respective one of the analyte detection means 110.

The planar body 105 can be configured in various ways. As shown, the planar body 105 is configured as a postcard including a portion for applying or displaying postage 125, a portion for applying or displaying a mailing address 130, and a portion for applying or displaying a return address 135. The mailing address 130 and/or the return address 135 can be printed directly on the planar body 105 or can be part of a label affixed to the planar body 105. The embodiment of the planar body 105 includes a first layer 140, a second layer 145, a third layer 150, and a fourth layer 155. The first layer 140, second layer 145, third layer 150, and fourth layer 155 can be assembled together in various ways, by lamination, use of adhesive or glue, heat sealing, stamping, crimping, ultrasonic welding, spin welding, or the use of various friction fittings, fasteners, clips, clamps, and other coupling means. One or more of the first layer 140, second layer 145, third layer 150, and fourth layer 155 can be configured as a support layer providing a majority of the bending strength of the planar body 105 while other layers can be configured with materials amenable to printing methods or suitable for marking or attachment of adhesive labels. The first layer 140 of the planar body 105 can include protrusions 160 within first apertures 165 that are configured to retain and enclose the analyte detection means 110 within the planar body 105. In the embodiment depicted, two protrusions 160 are positioned within each of three first apertures 165 to retain and enclose each of the analyte detection means 110 within the planar body 105. The second layer 145 of the planar body 105 includes second apertures 170 and the third layer 150 of the planar body 105 includes third apertures 175, where the second apertures 170 and the third apertures 175 are aligned with the first apertures 165. Optionally, a portion of the planar body 105 can be formed into a pocket portion, operable to retain paper instruction leaflets, for example bearing instructions specific to the analyte detection means 110 or the use of the planar body 105.

The analyte detection means 110 can include various aspects. In the embodiment depicted, the medical test card 100 includes three analyte detection means 110 where each of the analyte detection means 110 is the same, meaning each provides the colorimetric change when a portion thereof is contacted with the same analyte. It should be recognized that in other embodiments, each of the analyte detection means 110 can be different, meaning each provides the colorimetric change when a portion thereof is contacted with a different analyte. A seal 180 can be included that covers the analyte detection means 110. The seal 180 can be water resistant or water proof and can hermetically seal the analyte detection means 110 to optimize preservation of materials, fluids, reagents, enzymes, and/or various chemicals within the analyte detection means 110.

Figure 11:
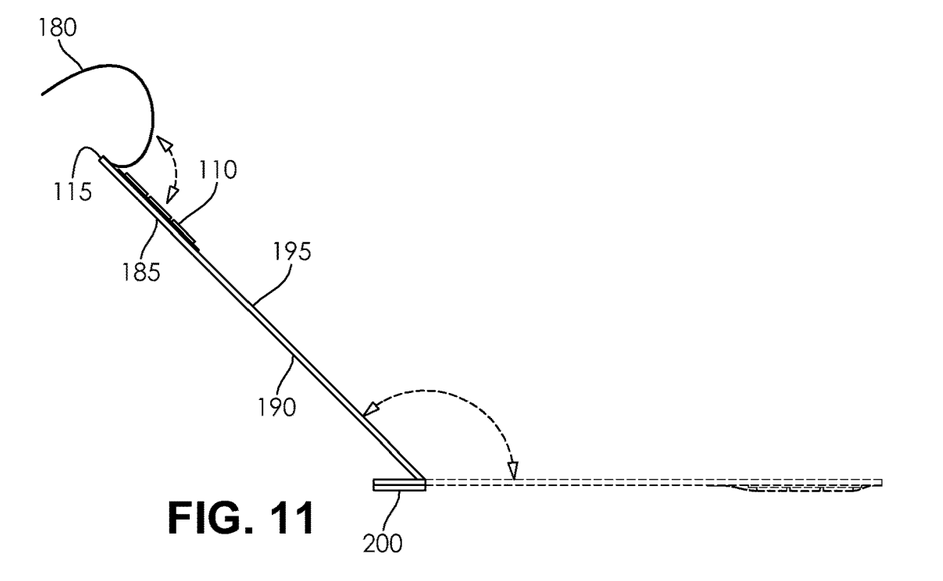
FIG. 11 is a side elevational view of the seal removed to expose the analyte detection means when the strip is pivoted away from a remainder of the medical test card.
Figure 12:
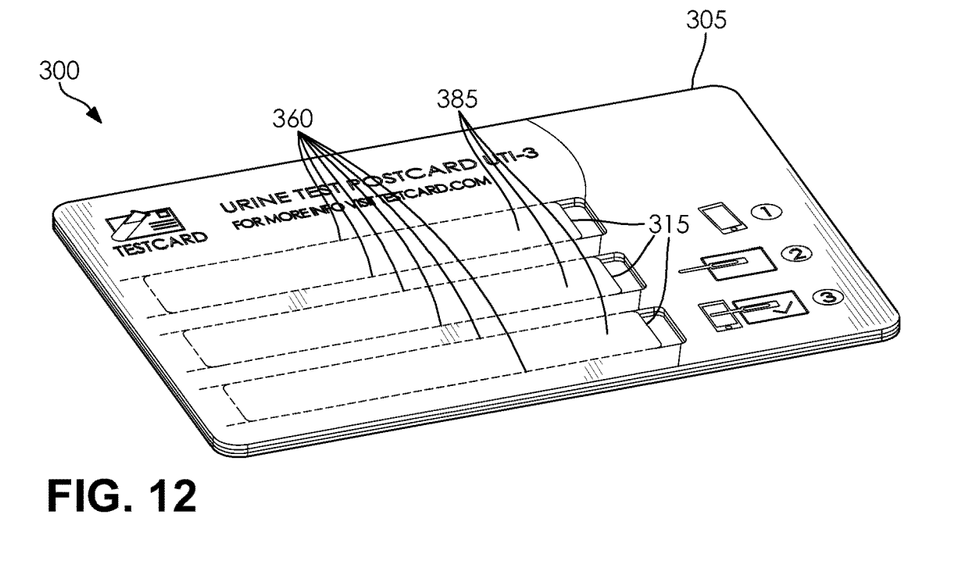
FIG. 12 is a front perspective view of a second embodiment of a medical test card according to the present technology.
Figure 13:
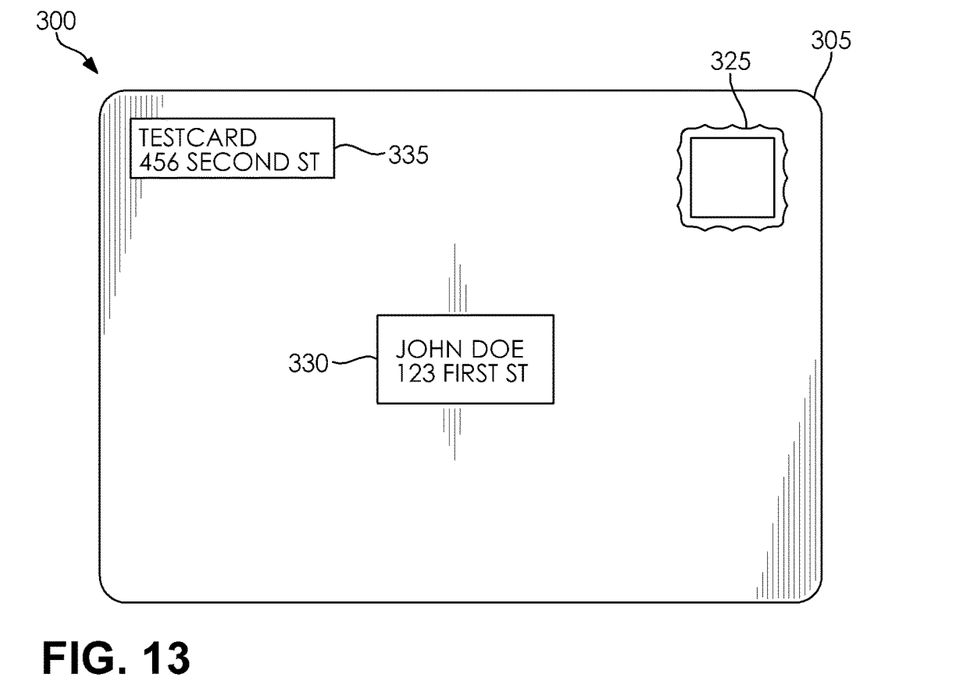
FIG. 13 is a rear elevational view thereof.
Figure 14:
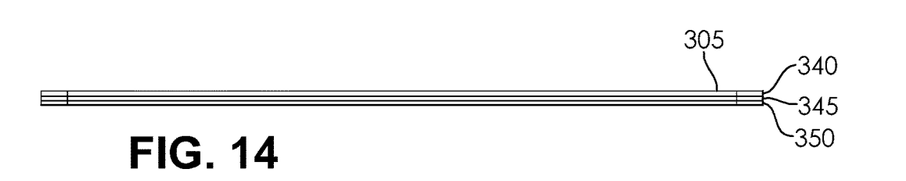
FIG. 14 is an end elevational view thereof.
Figure 15:
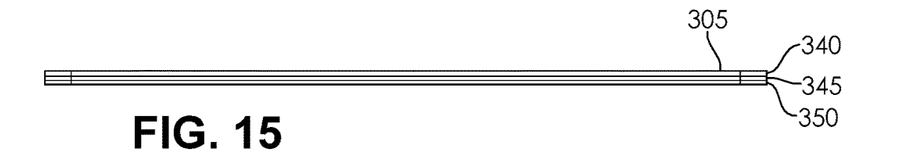
FIG. 15 is an end elevational view thereof, opposite that shown in FIG. 14.
Figure 16:
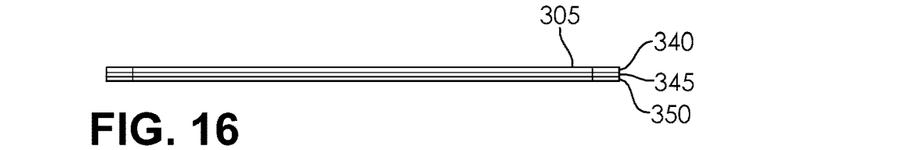
FIG. 16 is a left side elevational view thereof.
Figure 17:
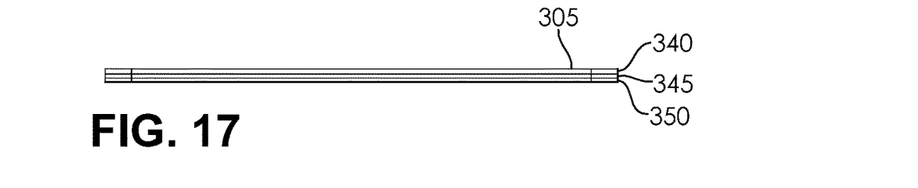
FIG. 17 is a right side elevational view thereof.
Figure 18:
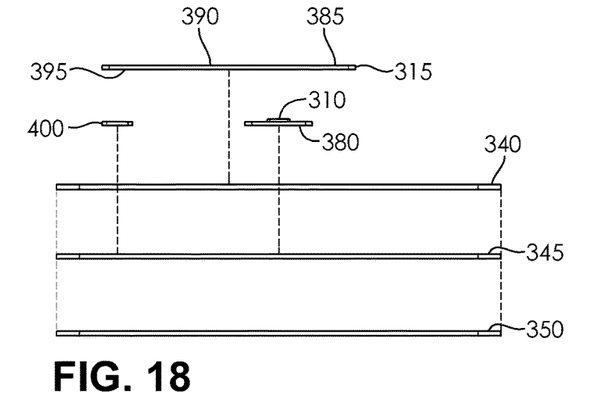
FIG. 18 is a side elevation exploded view.

The opening feature 115 can be configured in various ways. As shown, each opening feature 115 includes a pull tab 185. Operation of the opening feature 115 provides access to a strip 190 of the body 105 configured to extend from a remainder of the body 105, where the analyte detection means 110 is coupled to a face 195 of the strip 190 of the body 105. The opening feature 115 in the embodiment depicted can be opened by lifting the pull tab 185 so that the strip 190 pushes past the two protrusions 160 within the first aperture 165 of the first layer 140 of the planar body 105. The protrusions 160 can be resilient and deflect to allow the strip 190 to be extended from a remainder of the body 105. In other embodiments, the protrusions 160 can be frangible and can at least partially break off when the opening feature 115 is operated. As provided in the embodiment depicted, a retainer 200 serves to couple an end of the strip 190 opposite the pull tab 185 to the fourth layer 155 of the planar body 105. In this way, operation of the opening feature 115 by lifting the pull tab 185 can pivot the strip 190 past the protrusions 160 to extend away from a remainder of the body 105, where the retainer 200 retains a connection between the strip 190 and the remainder of the body 105. An example of such pivoting action is shown in FIG. 11. The retainer 200 can be selected to couple the strip 190 to the remainder of the planar body 105 in a permanent fashion. Or, the retainer 200 can be selected to couple the strip 190 to the remainder of the planar body 105 in a releasable fashion, for example where the retainer 200 includes a frangible material or a pressure sensitive adhesive, allowing the strip 190 to be detached from the remainder of the planar body 105. The seal 180 can be removed from the analyte detection means 110 after operation of the opening feature 115, whether or not the strip 190 is detached from the remainder of the planar body 105. The seal 180 can be formed of a foil or metallic material. The seal 180 can be operable to be pulled back or pulled off by a user.

Figure 1:
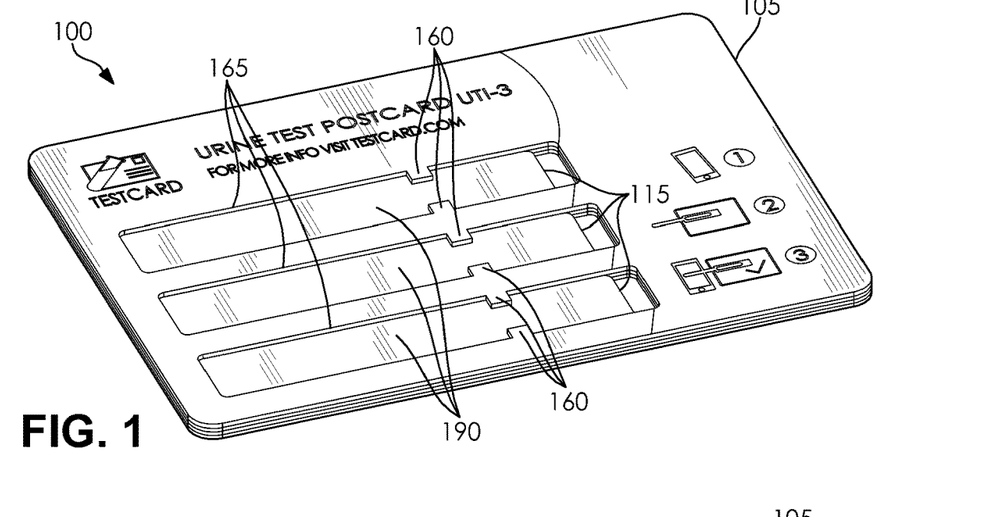
FIG. 1 is a front perspective view of a medical test card according to the present technology.
Figure 2:
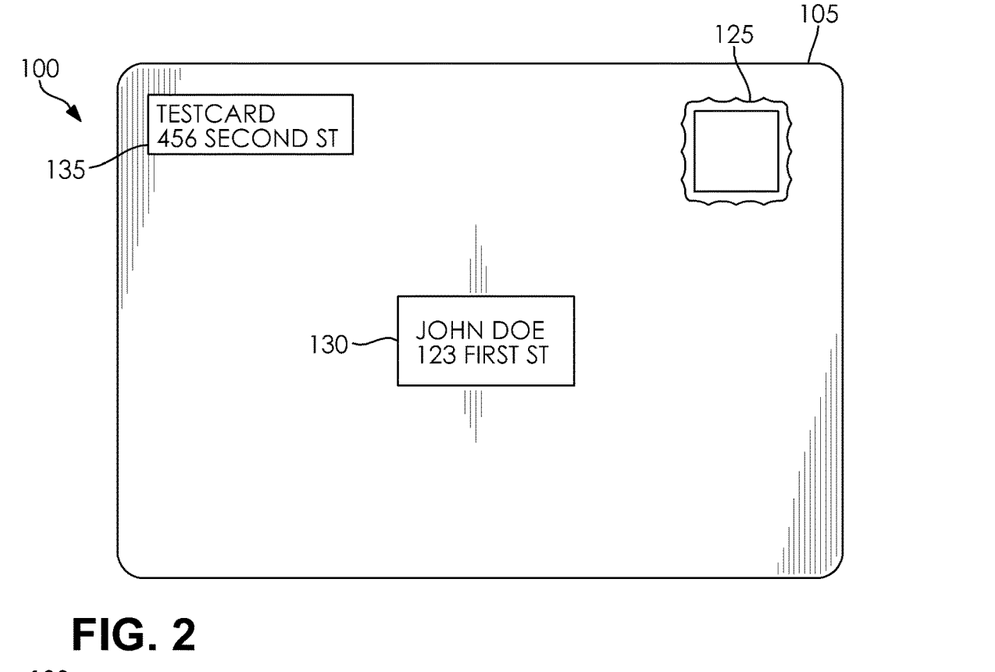
FIG. 2 is a rear elevational view thereof.
Figure 3:
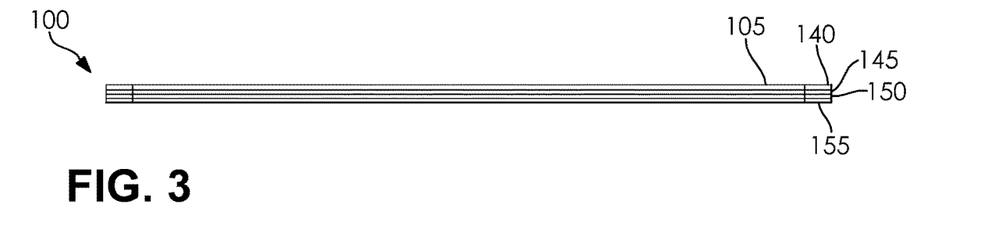
FIG. 3 is an end elevational view thereof.
Figure 4:
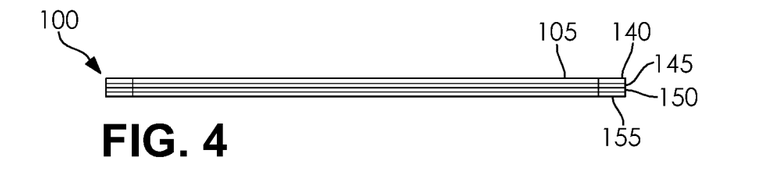
FIG. 4 is an end elevational view thereof, opposite that shown in FIG. 3.
Figure 5:
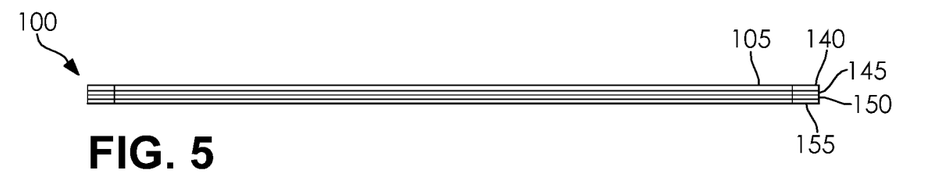
FIG. 5 is a left side elevational view thereof.
Figure 6:
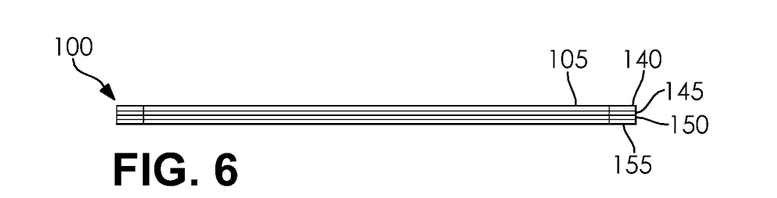
FIG. 6 is a right side elevational view thereof.
Figure 7:
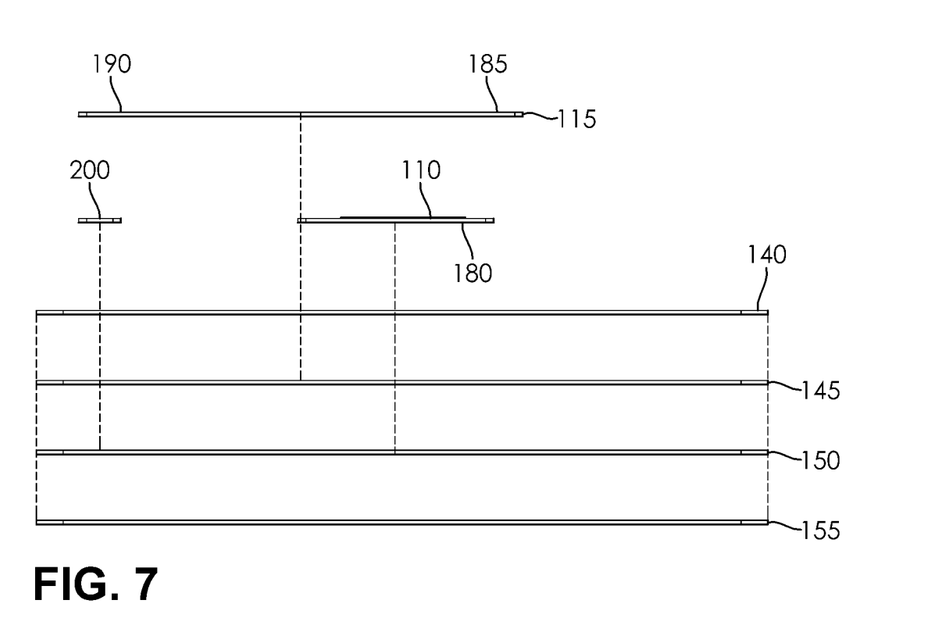
FIG. 7 is a side elevation exploded view.
Figure 8:
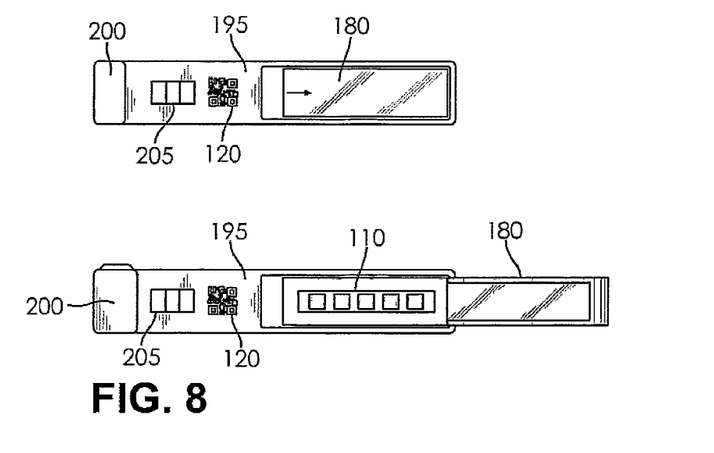
FIG. 8 is a view of a face of a strip removed from the medical test card, where a seal is removable to expose an analyte detection means.
Figure 9:
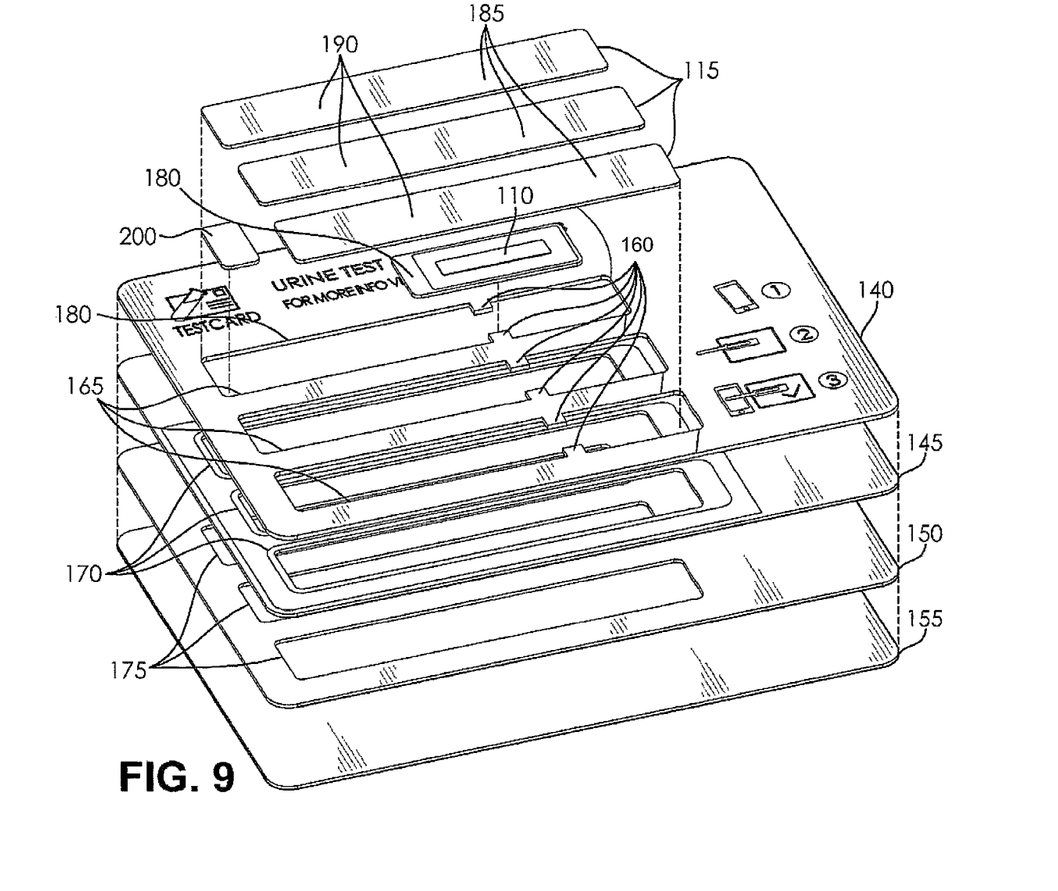
FIG. 9 is an exploded perspective view thereof.
Figure 10:
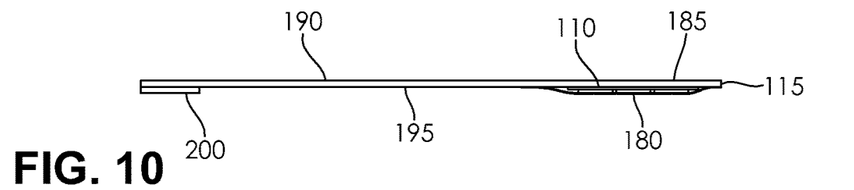
FIG. 10 is a side elevational view of the strip removed from the medical test card.

The optical code 120, in the embodiment depicted, is located on the face 195 of the strip 190 of the body 105. In this way, the optical code 120 can be read and captured in an image that also captures the analyte detection means 110. However, it should be noted that the optical code 120 including information identifying the analyte detection means 110 can be located elsewhere on the medical test card 100. As shown, the optical code 120 is configured as a QR code; however, the optical code 120 can be configured in other ways to identify the analyte detection means 110, including simply printed text describing the analyte detection means 110, the analyte of interest, and/or the nature of the diagnostic test the medical test card 100 is directed towards. Also located on the face 195 of the strip 190 of the body 105 is a reference standard 205 that can be used in quantifying the analyte. However, it should be noted that the reference standard 205 can be located elsewhere on the medical test card 100. The reference standard 205 can be included in the image of the optical code 120 and/or the analyte detection means 110. In this way, the image can be analyzed to compare any colorimetric change of the analyte detection means 110 with the reference standard 205 to quantify the analyte and report an amount of the analyte. For example, the reference standard 205 can include a series of colors corresponding to a series of analyte amounts or concentrations produced by the colorimetric change of the analyte detection means 110 when a portion thereof is contacted with the analyte.

With reference to FIGS. 12-22, a second embodiment a medical test card 300 is shown that includes a planar body 305, three analyte detection means 310, three opening features 315, and three optical codes 320. Each analyte detection means 310 is enclosed within the planar body 305. Each analyte detection means 310 is configured to provide a colorimetric change when a portion of the analyte detection means 310 is contacted with the analyte (e.g., a sample including the analyte). Each opening feature 315 in the planar body 305 is configured to provide access to a respective one of the analyte detection means 310 enclosed within the planar body 305. Each optical code 320 includes information identifying a respective one of the analyte detection means 310.

The planar body 305 can be configured in various ways. As shown, the planar body 305 is configured as a postcard including a portion for applying or displaying postage 325, a portion for applying or displaying a mailing address 330, and a portion for applying or displaying a return address 335. The mailing address 330 and/or the return address 335 can be printed directly on the planar body 305 or can be part of a label affixed to the planar body 305. The embodiment of the planar body 305 includes a first layer 340, a second layer 345, and a third layer 350. The first layer 340, second layer 345, and third layer 350, can be assembled together in various ways, by lamination, use of adhesive or glue, heat sealing, stamping, crimping, ultrasonic welding, spin welding, or the use of various friction fittings, fasteners, clips, clamps, and other coupling means. One or more of the first layer 340, second layer 345, and third layer 350 can be configured as a support layer providing a majority of the bending strength of the planar body 305 while other layers can be configured with materials amenable to printing methods or suitable for marking or attachment of adhesive labels. The first layer 340 of the planar body 305 can include perforations 360 or other frangible structures that are operable to tear and form first apertures 365 within the first layer 340. The perforations 360 are configured about areas of the first layer 340 that serve to retain and enclose the analyte detection means 310 within the planar body 305. In the embodiment depicted, the perforations 360 define the first apertures 365 that can be formed in the first layer 340, where three perforated areas of the first layer 340 retain and enclose a respective one of the three analyte detection means 310 within the planar body 305. The second layer 345 of the planar body 305 includes second apertures 370, where the second apertures 370 are aligned with the perforations 360 that define the first apertures 365 that can be formed in the first layer 340.

The analyte detection means 310 can include various aspects. In the embodiment depicted, the medical test card 300 includes three analyte detection means 310 where each of the analyte detection means 310 is the same, meaning each provides the colorimetric change when a portion thereof is contacted with the same analyte. It should be recognized that in other embodiments, each of the analyte detection means 310 can be different, meaning each provides the colorimetric change when a portion thereof is contacted with a different analyte. A seal 380 can be included that covers the analyte detection means 310. The seal 380 can be water resistant or water proof and can hermetically seal the analyte detection means 310 to optimize preservation of materials, fluids, reagents, enzymes, and/or various chemicals within the analyte detection means 310.

Figure 22:
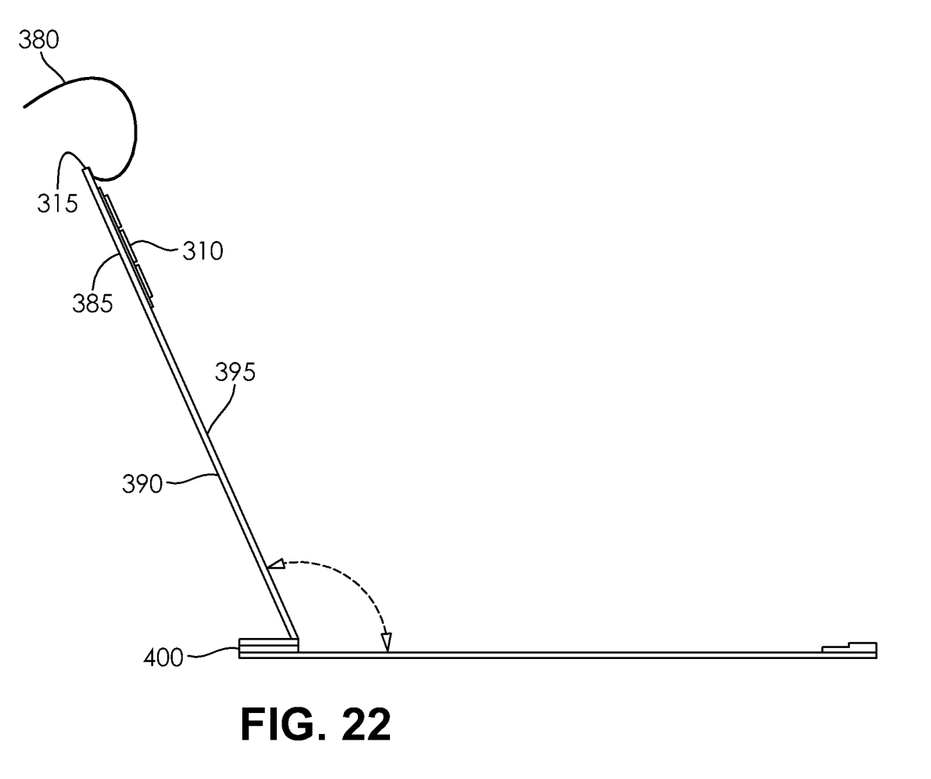
FIG. 22 is a side elevational view of the seal removed to expose the analyte detection means when the strip is pivoted away from a remainder of the medical test card.

The opening feature 315 can be configured in various ways. As shown, each opening feature 315 includes a pull tab 385. Operation of the opening feature 315 provides access to a strip 390 of the body 305 configured to extend from a remainder of the body 305, where the analyte detection means 310 is coupled to a face 395 of the strip 390 of the body 305. The opening feature 315 in the embodiment depicted can be opened by lifting the pull tab 385 so that the strip 390 is formed by tearing along the perforations 160 to form one of the first apertures 365 in the first layer 340 of the planar body 305. The perforations 360 can run to an end of the strip 390, allowing the strip 390 to be extended from a remainder of the body 305. In other embodiments, the perforations 360 can define an entire perimeter of the strip 390 in conjunction with the pull tab 385 to allow the entire strip 390 to be separated from the remainder of the first layer 340. As provided in the embodiment depicted, a retainer 400 serves to couple an end of the strip 390 opposite the pull tab 385 to the third layer 350 of the planar body 305. In this way, operation of the opening feature 315 by lifting the pull tab 185 and tearing the perforations 360 can pivot the strip 390 to extend away from a remainder of the body 305, where the retainer 400 retains a connection between the strip 390 and the remainder of the body 305. An example of such pivoting action is shown in FIG. 22. The retainer 400 can be selected to couple the strip 390 to the remainder of the planar body 305 in a permanent fashion. Or, the retainer 400 can be selected to couple the strip 390 to the remainder of the planar body 305 in a releasable fashion, for example where the retainer 400 includes a frangible material or a pressure sensitive adhesive, allowing the strip 390 to be detached from the remainder of the planar body 305. The seal 380 can be removed from the analyte detection means 310 after operation of the opening feature 315, whether or not the strip 390 is detached from the remainder of the planar body 305.

Figure 19:
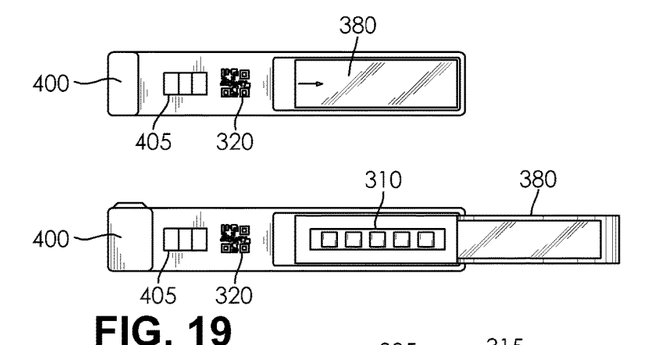
FIG. 19 is a view of a face of a strip removed from the medical test card, where a seal is removable to expose an analyte detection means.
Figure 20:
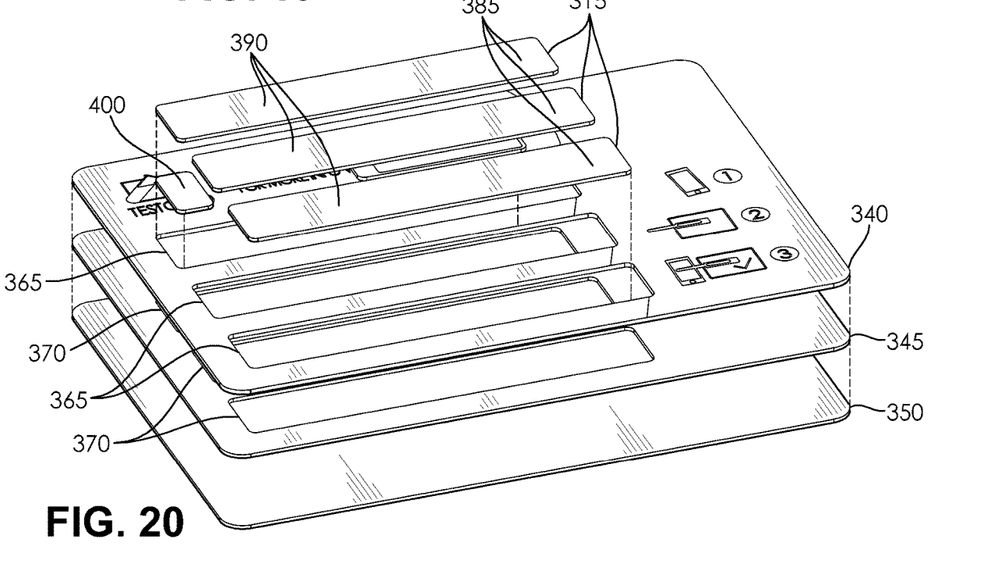
FIG. 20 is an exploded perspective view thereof.
Figure 21:
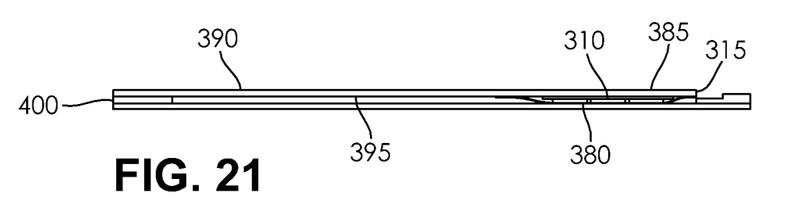
FIG. 21 is a side elevational view of the strip removed from the medical test card.

The optical code 320, in the embodiment depicted, is located on the face 395 of the strip 390 of the body 305. In this way, the optical code 320 can be read and captured in an image that also captures the analyte detection means 310. However, it should be noted that the optical code 320 including information identifying the analyte detection means 310 can be located elsewhere on the medical test card 300. As shown, the optical code 320 is configured as a QR code; however, the optical code 320 can be configured in other ways to identify the analyte detection means 310, including simply printed text describing the analyte detection means 310, the analyte of interest, and/or the nature of the diagnostic test the medical test card 300 is directed towards. Also located on the face 395 of the strip 390 of the body 305 is a reference standard 405 that can be used in quantifying the analyte. However, it should be noted that the reference standard 405 can be located elsewhere on the medical test card 400. The reference standard 405 can be included in the image of the optical code 320 and/or the analyte detection means 310. In this way, the image can be analyzed to compare any colorimetric change of the analyte detection means 310 with the reference standard 405 to quantify the analyte and report an amount of the analyte. For example, the reference standard 405 can include a series of colors corresponding to a series of analyte amounts or concentrations produced by the colorimetric change of the analyte detection means 310 when a portion thereof is contacted with the analyte.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A medical test card for detecting an analyte comprising: a planar body;
   an analyte detection means enclosed within the planar body, the analyte detection means configured to provide a colorimetric change when a portion of the analyte detection means is contacted with the analyte;
   an opening feature comprising a strip in the planar body, wherein the analyte detection means is coupled to a face of the strip, the strip having a pull tab which when lifted pivots the strip away from the planar body so that the strip extends from the planar body to provide access to the analyte detection means enclosed within the planar body to contact the analyte detection means with a sample; and
   an optical code including information identifying the analyte detection means.

2. The medical test card of claim 1, wherein the planar body is a postcard including a portion for applying or displaying postage and another portion for applying or displaying a mailing address.

3. The medical test card of claim 1, further comprising a plurality of the analyte detection means enclosed within the planar body.

4. The medical test card of claim 3, wherein each of the analyte detection means is the same.

5. The medical test card of claim 3, wherein each of the analyte detection means is different.

6. The medical test card of claim 3, further comprising a plurality of the opening features, each of the opening features configured to provide access to one of the analyte detection means enclosed within the planar body.

7. The medical test card of claim 1, further comprising a seal covering the analyte detection means coupled to the face of the strip of the body.

8. The medical test card of claim 1, wherein the strip of the body detaches from the remainder of the body.

9. The medical test card of claim 1, wherein the optical code is located on the face of the strip.

10. The medical test card of claim 9, further comprising a reference standard located on the face of the strip of the body.

11. A medical test card for detecting an analyte comprising:
    a planar body configured as a postcard including a portion for applying or displaying postage and another portion for applying or displaying a mailing address;
    an analyte detection means enclosed within the planar body, the analyte detection means providing a colorimetric change when a portion of the analyte detection means is contacted with the analyte;
    an opening feature comprising a strip in the planar body, wherein the analyte detection means is coupled to a face of the strip, the strip having a pull tab which when lifted pivots the strip away from the planar body so that the strip extends from the planar body to provide access to the analyte detection means enclosed within the planar body to contact the analyte detection means with a sample;

a seal covering the analyte detection means coupled to the face of the strip of the body;

an optical code including information identifying the analyte detection means located on the face of the strip of the body; and a reference standard located on the face of the strip of the body.

12. The medical test card of claim 11, further comprising a plurality of the analyte detection means enclosed within the planar body and a plurality of the opening features, each of the opening features configured to provide access to one of the analyte detection means enclosed within the planar body.

13. A method of detecting an analyte in a sample comprising:

providing a medical test card for detecting the analyte, the medical test card including:

a planar body;

an analyte detection means enclosed within the planar body, the analyte detection means configured to provide a colorimetric change when a portion of the analyte detection means is contacted with the analyte;

an opening feature comprising a strip in the planar body, wherein the analyte detection means is coupled to a face of the strip, the strip having a pull tab which when lifted pivots the strip away from the planar body so that the strip extends from the planar body to provide access to the analyte detection means enclosed within the planar body to contact the analyte detection means with a sample; and an optical code including information identifying the analyte detection means;

accessing the analyte detection means enclosed within the planar body using the opening feature; and contacting the analyte detection means with the sample.

14. The method of claim 13, further comprising:

reading the optical code using an imaging device to identify the analyte detection means; and imaging the analyte detection means following contact with the sample using the imaging device.

15. The method of claim 14, wherein the imaging device is a smartphone.

16. The method of claim 14, further comprising transmitting the image of the analyte detection means from the imaging device to a healthcare provider.

17. The method of claim 14, further comprising determining whether the image of the analyte detection means includes the colorimetric change and reporting detection of the analyte when the image of the analyte detection means includes the colorimetric change.

18. The method of claim 14, further comprising:

reading the optical code using an imaging device to identify the analyte detection means;

imaging the analyte detection means following contact with the sample and a reference standard located on a portion of the medical test card using the imaging device;

determining whether the image of the analyte detection means includes the colorimetric change; and when the colorimetric change is present, comparing the colorimetric change to the reference standard to quantify the analyte and reporting an amount of the analyte.

\* \* \* \* \*